ual Patent [19] [11] 4,088,630
Roos et al. [45] May 9, 1978

[54] CYCLIC ACETALS OF POLYOLS, THEIR PRODUCTION AND THEIR USE AS NON-DISCOLORING ANTI-OZONANTS

[75] Inventors: Ernst Roos, Odenthal-Osenau; Günter Langner, Leverkusen; Theo Kempermann, Cologne; Wolfgang Redetzky, Leverkusen, all of Germany

[73] Assignee: Bayer Aktiengesellschaft, Leverkusen, Germany

[21] Appl. No.: 735,394

[22] Filed: Oct. 26, 1976

[30] Foreign Application Priority Data

Oct. 31, 1975  Germany .............................. 2548911

[51] Int. Cl.² .................................................. C08K 5/15
[52] U.S. Cl. ............................... 260/45.8 A; 252/407; 260/28.5 B; 260/800; 526/295
[58] Field of Search ........ 260/45.8 A, 340.7, 340.9 R, 260/800; 526/295

[56] References Cited

U.S. PATENT DOCUMENTS

| | | |
|---|---|---|
| 3,072,679 | 1/1963 | Batzer et al. ................. 260/340.9 R |
| 3,625,913 | 12/1971 | Hunt ................................ 260/45.8 A |
| 3,632,550 | 1/1972 | D'Amico et al. ..................... 260/800 |
| 3,634,313 | 1/1972 | Sullivan et al. ................. 260/45.8 A |
| 3,721,682 | 3/1973 | Murai et al. ........................ 260/340.7 |
| 3,766,211 | 10/1973 | Batzer et al. ....................... 260/340.7 |
| 3,814,727 | 6/1974 | Hartmann et al. .............. 260/45.7 R |
| 3,926,912 | 12/1975 | Mayer-Mader et al. ............ 526/295 |

OTHER PUBLICATIONS

Warth, "The Chemistry and Technology of Waxes", 1956, pp. 750–752.

*Primary Examiner*—Donald E. Czaja
*Assistant Examiner*—R. A. White
*Attorney, Agent, or Firm*—Connolly and Hutz

[57] ABSTRACT

Cyclic acetals which may be obtained by reacting tri- to hexa-ols with tetrahydrobenzaldehydes can be used as non-discoloring stabilizers for natural and/or synthetic rubber against ozone attack.

41 Claims, No Drawings

CYCLIC ACETALS OF POLYOLS, THEIR PRODUCTION AND THEIR USE AS NON-DISCOLORING ANTI-OZONANTS

This invention relates to condensation products of tri-, tetra-, penta- and/or hexa-ols with tetrahydro-$\Delta^3$-benzaldehydes or endomethylene-tetrahydro-$\Delta^3$-benzaldehydes in a molar ratio of 1:1 to 1:3, in which all the aldehyde groups are present in fully acetalated form.

The invention also relates to a process for producing the condensation products, to their use as anti-ozonants in natural and/or synthetic rubber and to the rubbers stabilised with the anti-ozonants.

The following alcohols with 3, 4, 5 or 6 hydroxyl groups are mentioned as examples of triols, tetraols, pentaols and hexaols: glycerol, 1,1,1-trimethylol ethane, 1,1,1-trimethylol propane, 1,1,1-trimethylol butane, 1,2,6-hexane triol, pentaerythritol, sorbitol, mannitol and 2,2,6,6-tetramethylol cyclohexanol.

Tetrahydro-$\Delta^3$-benzaldehydes and endomethylene-tetrahydro-$\Delta^3$-benzaldehydes are compounds corresponding to the following formulae:

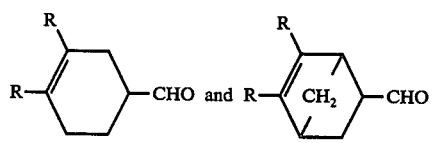

in which R represents a hydrogen or a methyl group. The following are mentioned as examples of these compounds: tetrahydro-$\Delta^3$-benzaldehyde, 3-methyl tetrahydro-$\Delta^3$-benzaldehyde, 4-methyltetrahydro-$\Delta^3$-benzaldehyde, 3,4-dimethyltetrahydro-$\Delta^3$-benzaldehyde, 2,5-endomethylene-tetrahydro-$\Delta^3$-benzaldehyde, 2,5-endomethylene-3-methyl-tetrahydro-$\Delta^3$-benzaldehyde, 2,5-endomethylene-4-methyl-tetrahydro-$\Delta^3$-benzaldehyde, 2,5-endomethylene-3,4-dimethyl-tetrahydro-$\Delta^3$-benzaldehyde.

The condensation products of triols, pentaols and hexaols, for example glycerol, 1,1,1-trimethylolethane, 1,1,1-trimethylol-propane, 2,2,6,6-tetramethylol cyclohexanol, 1,2,6-hexanetriol, sorbitol or mannitol, with the tetrahydro-$\Delta^3$-benzaldehydes in a molar ratio of from 1:1 to 1:3, are mixtures of substances.

This is illustrated with reference to the example of glycerol:

The condensation of glycerol with tetrahydro-$\Delta^3$-benzaldehyde in a molar ratio of 1:1 up to a molar ratio of 1:1.5 (equivalent to 2:3) results in the formation of mixtures containing the following 1,3-dioxanes and 1,3-dioxolanes:

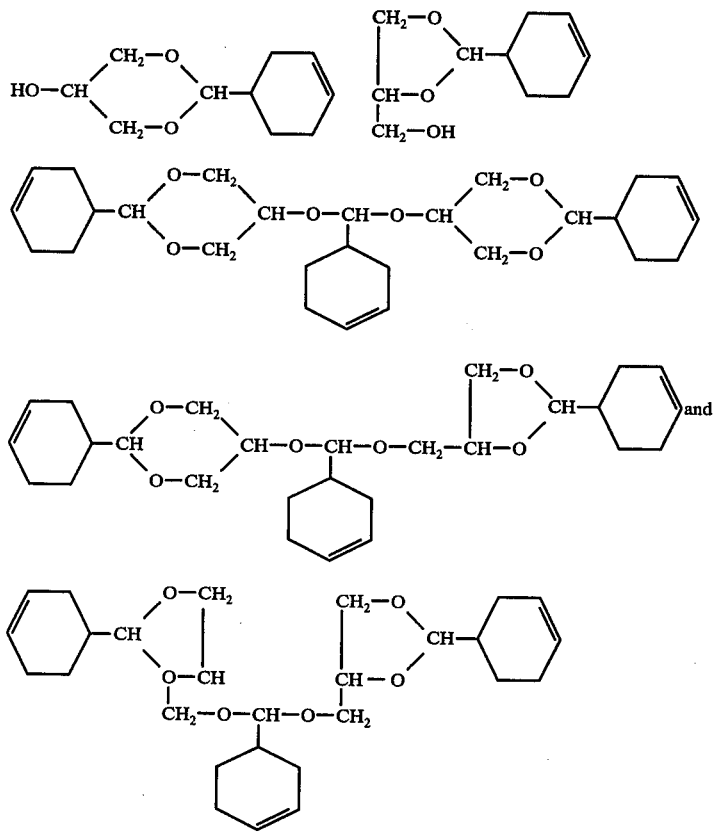

Condensation of the other triols mentioned results in corresponding mixtures.

In the condensation of the pentahydroxy or hexahydroxy compounds with tetrahydro-$\Delta^3$-benzaldehydes in a molar ratio of 1:1 to 1:3, the number of the corresponding isomeric cyclic acetals is of course even greater.

The condensation of pentaerythritol with 2 moles of tetrahydro-$\Delta^3$-benzaldehydes results in the formation of defined bis-acetals corresponding to the formulae:

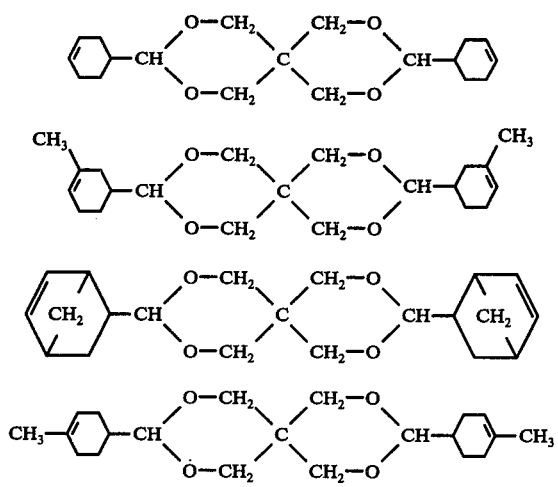

Generally, it may be said that the following condensation products are possible:
(a) triol-aldehyde condensation products in molar ratios of 1:1 and 1:1.5
(b) tetraol-aldehyde condensation products in molar ratios of 1:1 and 1:2
(c) pentaol-aldehyde condensation products in molar ratios of 1:1, 1:1.5, 1:2 and 1:2.5 and
(d) hexaol-aldehyde condensation products in molar ratios of 1:1, 1:2 and 1:3.

Condensation of the above-mentioned polyols with the tetrahydro-Δ³-benzaldehydes may be carried out similarly by the methods normally used for the acetalation of alcohols with aldehydes.

The polyhydroxyl compound is reacted with the aldehyde in the presence of catalytic quantities of an acid dehydration catalyst at temperatures in the range from 0 to 200° C and preferably at temperatures in the range from 20 to 120° C, from 1 to 3 moles of aldehyde being used per mole of alcohol.

The reaction may be carried out either in the presence or absence of solvents. Suitable solvents are both polar solvents, such as methanol, ethanol, or dioxane, and apolar solvents such as petrol, benzene or toluene. In cases where water-immiscible solvents are used, they may optionally be used for the azeotropic distillation of the water formed during the condensation reaction.

HCl, $ZnCl_2$, $H_2SO_4$, benzene sulphonic acid, naphthalene sulphonic acid and p-toluene sulphonic acid are mentioned as examples of acid dehydration catalysts, p-toluene sulphonic acid being preferred.

The catalysts are preferably used in a quantity of from 0.05 to 5% by weight and, with particular preference, in a quantity of from 0.1 to 1% by weight, based on the aldehyde.

The condensation products according to the invention may be added to natural and/or synthetic rubbers in order to stabilise them against degradation by ozone.

It is known that utility articles produced from natural and/or synthetic rubbers by vulcanisation develop cracks when their surface is under mechanical stress and, at the same time, exposed to ozone.

A significant increase in the useful life of these rubber articles can be obtained by adding derivatives of p-phenylene diamine, such as N-phenyl-N'-isopropyl-p-phenylene diamine for example, to the rubber in relatively small quantities. Unfortunately, all the hitherto known, active compounds of this kind have a discolouring effect in light, so that they can only be used in articles containing carbon black. In addition to this restriction, however, there is the further restriction that it is only possible to use these compounds in carbon-black-containing articles of the kind in whose case there is no danger of any contact discoloration of adjoining materials. It is also known that certain wax combinations can be used for improving the resistance to ozone of light-coloured articles. Although these combinations have a certain protective effect, they can only develop that effect providing the protective film of wax formed on the surface of the article remains completely intact. Under dynamic stressing, however, the film readily breaks up and the ozone cracks subsequently formed at these faults are generally deeper and wider than those formed in the absence of the wax film. However, even if the wax film remains intact, protection is incomplete because a small quantity of ozone passes through the film and, in doing so, causes cracks to be formed.

German Auslegeschrifts Nos. 1,693,163 and 1,917,600, also German Offenlegungsschrift No. 1,668,091, describe enolethers corresponding to the formula

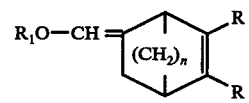

in which $R_1$ represents the radical of an alcohol, n = 0 or 1 and R represents a hydrogen atom or a methyl group, and also their use as non-discolouring antiozonants.

Compared with these enolethers, the condensation products according to the invention are more effective as antiozonants, show lower volatility and are odourless. Thus, they impart an increased service life, in addition to a lack of odour, to the rubber mixtures to be protected against degradation.

The condensation products according to the invention may readily be dispersed in rubber mixtures and may be used in conjunction with the rubber chemicals normally employed (for example vulcanisation accelerators, vulcanising agents, antiagers, plasticisers, fillers, waxes, dyes, etc.) without interfering in any way with their specific effects.

The condensation products according to the invention are added to the rubber in such quantities that the rubber is stabilised against degradation by ozone. The appropriate quantities are known to, or may readily be determined by, the average expert.

The quantity in which the new products are used in polychloroprene rubber is, for example, between 0.1 and 6.0% by weight and preferably between 0.3 and 3.0% by weight, based on the polymer content which consists of 100.0% by weight of polychloroprene or polychloroprene with a covulcanisable rubber, the minimum polychloroprene content being 20% by weight and preferably 30% by weight.

Suitable rubbers covulcanisable with polychloroprene are, for example, natural rubber or synthetic rubber-like polymers which contain double bonds and which are obtained, for example, from conjugated diolefins, such as butadiene, dimethyl butadiene, isoprene and its homologues, or copolymers of these conjugated diolefins with polymerisable vinyl compounds, for example, styrene, α-methyl styrene, acrylonitrile, methacrylonitrile, acrylates and methacrylates.

In cases where the condensation products according to the invention are added to rubbers other than the above-mentioned polychloroprenes, it is advisable to combine them with waxes because combinations such as these have a synergistic effect.

The ratio by weight of wax to the condensation products according to the invention may vary within wide limits although it is preferably between 0.25 and 2.5:1.

The waxes consist at least partly of microcrystalline paraffins. Macrocrystalline paraffins are paraffins whose refractive index $n_D^{100}$ is lower than that calculated in accordance with the equation: $n_D^{100} = 0.00035 t + 1.4056$ where $t$ = solidification point in ° C, whereas microcrystalline paraffins are paraffins whose refractive index is higher than that calculated in accordance with the above formula (cf. the definition of petroleum waxes in Proceedings of ASTM-TAPPI Symposium on Petroleum Waxes, Feb. 63, TAPPI-STAP No. 2, pages 1 to 19).

The following are examples of combinations of the cyclic acetals of polyols according to the invention and waxes: 4 parts by weight of the condensation product of pentaerythritol and tetrahydro-$\Delta^3$-benzaldehyde in a molar ratio of 1:2 + 2.0 parts by weight of microcrystalline paraffin; 4 parts by weight of the condensation product of pentaerythritol and 2,5-endomethylenetetrahydro-$\Delta^3$-benzaldehyde in a molar ratio of 1:2 + 1 part by weight of microcrystalline paraffin.

Suitable rubbers are natural rubber or, in addition to polychloroprene, synthetic rubber-like polymers which still contain double bonds and which are obtained for example from conjugated diolefins, such as butadiene, dimethyl butadiene, isoprene and its homologues, or copolymers of these conjugated diolefins with polymerisable vinyl compounds, such as styrene, α-methyl styrene, acrylonitrile, methacrylonitrile, acrylates and methacrylates.

The synergistically acting antiozonant wax combination is added to the rubbers in such quantities that the rubbers are stabilised against degradation by ozone. The appropriate quantities are known to, or may readily be determined by, the average expert. The quantity added amounts for example to between 0.5 and 5% by weight and preferably to between 1 and 10% by weight, based on the polymer content.

The invention is illustrated by, but by no means limited to, the following Examples:

EXAMPLE 1

Condensation product of glycerol and tetrahydro-$\Delta^3$-benzaldehyde in a molar ratio of 1:1

92 g (1mole) of glycerol, 110 g (1 mole) of tetrahydro-$\Delta^3$-benzaldehyde and 1 g of p-toluene sulphonic acid in 400 ml of cleaning spirit were boiled under nitrogen in a water separator until 18 ml of water had separated off. The mixture was stirred with 3 g of calcium hydroxide, filtered and distilled in vacuo at 15 mm/100° C. The residue was distilled in vacuo. Yield: 157 g = 85.5% of the theoretical yield, colourless oil, b.p.$_{11mm}$/144–152° C, $n_D^{20}$: 1.4970.

$C_{10}H_{16}O_3$ calculated: C, 65.22; H, 8.70; O, 26.09. MW 184 observed: C, 65.8; H, 8.4; O 25.8.

EXAMPLE 2

Condensation product of 1,1,1-trimethylolethane and tetrahydro-$\Delta^3$-benzaldehyde in a molar ratio of 1:1

The procedure was as described in Example 1, except that 120 g (1 mole) of 1,1,1-trimethylolethane were used instead of 92 g of glycerol. Yield: 210 g = 99% of the theoretical yield, colourless oil, $n_D^{20}$: 1.4960, which solidifies into colourless, low melting crystals.

EXAMPLE 3

Condensation product of 1,1,1-trimethylolpropane and tetrahydro-$\Delta^3$-benzaldehyde in a molar ratio of 1:1

The procedure was as described in Example 1, except that 134 g (1 mole) of 1,1,1-trimethylolpropane were used instead of 92 g of glycerol. Yield 158 g = 75% of the theoretical yield, colourless oil, b.p.$_{0.04}$/115°–120° C which solidifies into colourless crystals melting at 42° C.

$C_{13}H_{22}O_3$ calculated: C, 69.03; H, 9.73; O, 21.24. MW 226 observed: C, 68.4; H, 9.7; O, 21.4.

EXAMPLE 4

Condensation product of glycerol and tetrahydro-$\Delta^3$-benzaldehyde in a molar ratio of 2:3

92 g (1 mole) of glycerol, 165 g (1.5 mole) of tetrahydro-$\Delta^3$-benzaldehyde and 1 g of p-toluene sulphonic acid in 400 ml of cleaning spirit were boiled under nitrogen in a water separator until 27 ml of water had separated off. The mixture was stirred with 3 g of calcium hydroxide, filtered and distilled first in a vacuum at 15 ml/100° C and then in a high vacuum at 1 mm/100° C. Yield: 222 g = 96.5% of the theoretical yield, almost colourless viscous oil, $n_D^{20}$: 1.5099

$C_{27}H_{40}O_6$ calculated: C, 70.43; H, 8.70; O, 20.87. MW 460 Observed: C, 69.9; H, 8.4; O, 21.4.

EXAMPLE 5

Condensation product of 1,1,1-trimethylolethane and tetrahydro-$\Delta^3$-benzaldehyde in a molar ratio of 2:3

The procedure was as described in Example 4, except that 120 g (1 mole) of 1,1,1-trimethylolethane were used instead of 92 g of glycerol. Yield: 255 g = 99% of the theoretical yield, brownish viscous oil, $n_D^{20}$: 1.5067.

EXAMPLE 6

Condensation product of 1,1,1-trimethylolpropane and tetrahydro-$\Delta^3$-benzaldehyde in a molar ratio of 2:3

The procedure was as described in Example 4, except that 134 g (1 mole) of 1,1,1-trimethylolpropane were used instead of 92 g of glycerol. Yield: 248 g = 89.5% of the theoretical yield, brownish viscous oil.

$C_{33}H_{56}O_6$ calculated: C, 72.80; H, 9.56; O, 17.65. MW 544 observed: C, 72.4; H, 9.5; O, 17.7.

EXAMPLE 7

Condensation product of pentaerythritol and tetrahydro-$\Delta^3$-benzaldehyde in a molor ratio of 1:2

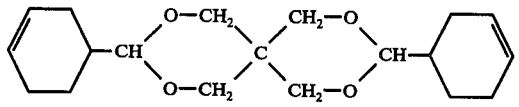

136 g (1 mole) of pentaerythritol, 220 g (2 moles) of tetrahydro-$\Delta^3$-benzaldehyde and 2 g of p-toluene sulphonic acid in 300 ml of toluene were boiled under nitrogen in a water separator until 36 ml of water had separated off. The solvent was distilled off in vacuo at 15 mm/100° C and the residue was recrystallised from methanol. Yield: 277 g = 86.5% of the theoretical yield, colourless crystals melting at 93-95° C $C_{19}H_{28}O_4$ calculated: C 71.25; H, 8.75; O, 20.00. MW 320 observed: C 71.5; H 9.1; O, 19.8.

The same product was obtained when no solvent is used; when cleaning spirit was used instead of toluene; or when the condensation reaction was carried out in methanol without separating off the water formed.

EXAMPLE 8

Condensation product of pentaerythritol and a mixture of 3-methyl- and 4-methyl-tetrahydro-$\Delta^3$-benzaldehyde in a molar ratio of 1:2

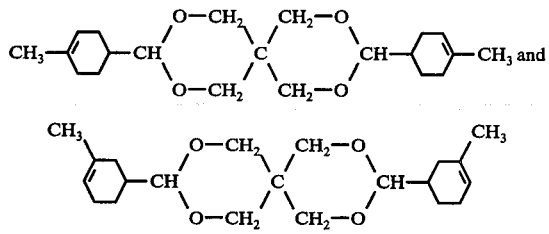

136 g (1 mole) of pentaerythritol, 248 g (2 moles) of 3- and 4-methyl-tetrahydro-$\Delta^3$-benzaldehyde and 2 g of p-toluene sulphonic acid in 400 ml of washing spirit were boiled under nitrogen in a water separator until 36 ml of water had separated off. Removal of the solvent by distillation in vacuo at 15 mm/100° 1 C gave a partially crystallised mass in a quantitative yield. Colourless crystals melting at 111° to 113° C were obtained by recrystallisation from methanol.

$C_{21}H_{32}O_4$ calculated: C, 72.42; H, 9.20; O, 18.39. MW 348 observed: C, 72.0; H, 9.6; O, 18.6.

EXAMPLE 9

Condensation product of pentaerythritol and 2,5-endomethylene-tetrahydro-$\Delta^3$-benzaldehyde in a molar ratio of 1:2

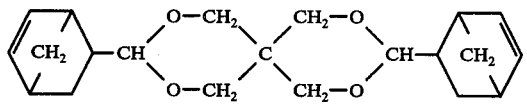

34 g (0.25 mole) of pentaerythritol, 61 g (0.5 mole) of 2,5-endomethylene tetrahydro-$\Delta^3$-benzaldehyde and 1 g of p-toluene sulphonic acid were boiled under reflux for 4 hours in 300 ml of methanol. The suspension was filtered under suction at 5° C and dried, giving 48 g = 56% of the theoretical yield of colourless crystals melting at 219°-223° C.

$C_{21}H_{28}O_4$ calculated: C, 73.25; H, 8.14; O, 18.60. MW 344 observed: C, 73.1; H, 8.0; O, 18.4.

The same product was obtained when the condensation reaction is carried out in 300 ml of cleaning spirit or toluene instead of 300 ml of methanol, and the water formed separated off.

EXAMPLE 10

Condensation product of sorbtiol and tetrahydro-$\Delta^3$-benzaldehyde in a molar ratio of 1:2

91 g (0.5 mole) of sorbitol, 110 g (1 mole) of tetrahydro-$\Delta^3$-benzaldehyde and 1 g of p-toluene sulphonic acid were boiled under reflux for 5 hours in 300 ml of methanol. The solvent was distilled off first in a vacuum at 15 mm/100° C and then in a high vacuum at 1 mm/100° C. Yield: 183 g = 100% of the theoretical yield of a highly viscous, brownish oil $C_{20}H_{30}O_6$ calculated: C, 65.57; H, 8.19; O, 26.23. MW 366 observed: C, 65.5; H, 8.3; O, 27.0.

EXAMPLE 11

Condensation product of sorbitol and tetrahydro-$\Delta^3$-benzaldehyde in a molar ratio of 1:3

91 g (0.5 mole) of sorbitol, 165 g (1.5 mole) of tetrahydro-$\Delta^3$-benzaldehyde and 1 g of p-toluene sulphonic acid were boiled under reflux for 5 hours in 400 ml of methanol. The solvent was removed in a vacuum at 15 mm/100° C and then in a high vacuum at 1 mm/100° C. Yield 223 g = 97.5% of the theoretical yield, highly viscous, brownish oil $C_{27}H_{38}O_6$ calculated: C, 70.59; H, 8.49; O, 20.92. MW 458 observed: C, 70.0; H, 8.5; O, 20.9.

EXAMPLE 12

Condensation product of mannitol and tetrahydro-$\Delta^3$-benzaldehyde in a molar ratio of 1:3.

The procedure was as described in Example 11, except that 91 g of mannitol were used instead of 91 g of sorbitol. Yield: 227 g = 99% of the theoretical yield of a highly viscous, yellowish oil.

$C_{27}H_{38}O_6$ calculated: C, 70.59; H, 8.49; O, 20.92. MW 458 observed: C, 70.6; H, 8.7; O, 20.8.

EXAMPLE 13

The following rubber mixture was prepared on mixing rolls:

| | |
|---|---|
| Polychloroprene | 100.0 |
| Magnesium oxide | 4.0 |
| Stearic acid | 0.5 |
| Precipitated silica (BET-value 180 m²/g): | 20.0 |
| Soft kaolin | 170.0 |
| Titanium dioxide | 5.0 |
| Antimony pentoxide | 5.0 |
| Naphthenic petroleum plasticiser | 20.0 |
| Chloroparaffin | 10.0 |
| Ethylene thiourea | 1.2 |
| Zinc oxide | 5.0 |
| Antiozonants according to Tables 1 and 2. | |

Test specimens measuring 0.4 × 4.5 × 4.5 cm and 0.4 × 4.5 × 5.5 cm were vulcanised from these mixtures (press vulcanisation for 30 minutes at 151° C).

4 each of these test specimens were then clamped in a plastic frame in such a way that elongations of 10, 20, 35 and 60% were obtained at their surfaces. The stretched test specimens were then exposed at room temperature to a stream of air containing 1000 parts of ozone to 100 million parts of air. The test specimens were visually inspected for cracks after intervals of 2, 4, 6, 8, 24, 48, 72, 96 and 168 hours. The figures quoted in the Tables represent the periods of time elapsing before the first cracks were observed. The tests were terminated after 168 hours.

Table 1:

| Elongation in % | | 10 | 20 | 35 | 60 |
|---|---|---|---|---|---|
| without antiozonant (comparison) | | 24 | 8 | 4 | 4 |
| condensation product of pentaerythritol and tetrahydro-$\Delta^3$-benzaldehyde in a ratio of 1:2 | 0.25 part by weight | >168 | >168 | 8 | 8 |
| | 0.5 part by weight | >168 | >168 | >168 | >168 |
| | 1.0 part | >168 | >168 | >168 | >168 |

Table 1:-continued

| Elongation in % without antiozonant (comparison) | 10 | 20 | 35 | 60 |
|---|---|---|---|---|
| | 24 | 8 | 4 | 4 |
| by weight | | | | |

Table 2:

| Elongation in % without antiozonant (comparison) | | 10 | 20 | 35 | 60 |
|---|---|---|---|---|---|
| | | 8 | 8 | 4 | 2 |
| condensation product of pentaerythritol and 2,5-endo-methylene-tetrahydro-$\Delta^3$-benzaldehyde in a molar ratio of 1:2 | 0.25 part by weight | >168 | 24 | 6 | 2 |
| | 0.5 part by weight | >168 | >168 | 8 | 8 |
| | 1.0 part by weight | >168 | >168 | >168 | >168 |

Table 3:

| Elongation in % without antiozonant (comparison) | | 10 | 20 | 35 | 60 |
|---|---|---|---|---|---|
| | | 8 | 4 | 2 | 2 |
| condensation product of pentaerythritol and a mixture of 3- and 4-methyl-tetra-$\Delta^3$-benzaldehyde in a molar ratio of 1:2 | 1.0 part by weight | >168 | >168 | >168 | 4 |

EXAMPLE 14

The following rubber mixture was prepared on mixing rolls:

| | |
|---|---|
| Polychloroprene | 35.0 |
| Styrene-butadiene copolymer | 65.0 |
| Titanium dioxide | 10.0 |
| Air-classified hard kaolin | 30.0 |
| Precipitated silica (BET-value 180 m²/g) | 20.0 |
| Zinc oxide | 5.0 |
| Magnesium oxide | 2.0 |
| Diethylene glycol | 1.0 |
| Dibenzothiazyl disulphide | 1.0 |
| Tetramethyl thiuram monosulphide | 0.2 |
| Sulphur | 1.4 |
| Naphthenic mineral oil plasticiser | 5.0 |
| Stearic acid | 1.0 |
| Ethylene thiourea | 0.25 |
| Antiozonant, cf. Table 4 | |

Test specimens measuring 0.4 × 4.5 × 4.5 and 0.4 × 4.5 × 5.5 cm were vulcanised from this mixture (press vulcanisation for 30 minutes at 150° C). The test conditions were the same as described in Example 13, except that the stream of air contained 400 instead of 1000 parts of ozone to 100 million parts of air.

Table 4:

| Elongation in % without antiozonant (comparison) | | 10 | 20 | 35 | 60 |
|---|---|---|---|---|---|
| | | 4 | <2 | <2 | <2 |
| condensation product of pentaerythritol and tetrahydro-$\Delta^3$-benzaldehyde in a molar ratio of 1:2 | 1.0 part by weight | >168 | >168 | 4 | 2 |
| | 2.0 part by weight | >168 | >168 | >168 | >168 |

Table 4:-continued

| Elongation in % without antiozonant (comparison) | 10 | 20 | 35 | 60 |
|---|---|---|---|---|
| | 4 | <2 | <2 | <2 | a molar ratio of 1:2

EXAMPLE 15

The following rubber mixture was prepared on mixing rolls:

| | |
|---|---|
| Polychloroprene | 50.0 |
| Light crepe rubber | 50.0 |
| Titanium dioxide | 50.0 |
| Zinc oxide | 70.0 |
| Stearic acid | 1.0 |
| Sulphur | 1.0 |
| Dibenzothiazyl disulphide | 0.5 |
| Tetramethyl thiuram monosulphide | 0.2 |
| Ethylene thiourea | 0.7 |
| Magnesium oxide | 2.0 |
| Ultramarine blue | 0.02 |
| Antiozonant, cf. Table 5 | |

Test specimens measuring 0.4 × 4.5 × 4.5 cm and 0.4 × 4.5 × 5.5 cm were vulcanised from this mixture (press vulcanisation for 30 minutes at 150° C).

The test conditions were as described in Example 13, except that the stream of air contained 400 instead of 1000 parts of ozone per 100 million parts of air.

Table 5

| Elongation in % without antiozonant (comparison) | | 10 | 20 | 35 | 60 |
|---|---|---|---|---|---|
| | | >168 | 96 | 8 | 6 |
| condensation product of pentaerythritol and tetrahydro-$\Delta^3$-benzaldehyde in a molar ratio of 1:2 | 1.0 part by weight | >168 | >168 | 8 | 8 |
| | 2.0 part by weight | >168 | >168 | >168 | >168 |

EXAMPLE 16

The following rubber mixture was prepared on mixing rolls:

| | |
|---|---|
| Natural rubber | 100.0 |
| Zinc oxide | 10.0 |
| Precipitated chalk | 160.0 |
| Stearic acid | 0.7 |
| Titanium dioxide, anatase | 10.0 |
| Dibenzothiazyl disulphide | 1.0 |
| Hexamethylene tetramine | 0.25 |
| Sulphur | 2.2 |
| Antiozonant, cf. Tables 6 and 7 | |
| Antiozonant wax. cf. Tables 6 and 7 | |

Test specimens measuring 0.4 × 4.5 × 4.5 cm and 0.4 × 4.5 × 5.5 cm were vulcanised from these mixtures (press vulcanisation for 30 minutes at 140° C). The test conditions were as described in Example 13, except that the ozone concentration amounted to 50 instead of 1000 parts of ozone per 100 million parts of air.

Table 6

| Elongation in % | | | 10 | 20 | 35 | 60 |
|---|---|---|---|---|---|---|
| a) | without antiozonant/ without antiozonant wax (comparison) | | <2 | <2 | <2 | <2 |
| b) | antiozonant wax (comparison) | 2.0 parts by weight | >168 | 24 | 8 | 8 |
| c) | condensation product of pentaerythritol and tetrahydro-$\Delta^3$-benzaldehyde in a molar ratio of 1:2 (comparison) | 4.0 parts by weight | <2 | <2 | <2 | <2 |
| d) | same condensation | 4.0 parts | >168 | >168 | 72 | 8 |

Table 6-continued

| Elongation in % | | 10 | 20 | 35 | 60 |
|---|---|---|---|---|---|
| | product as c) + anti-ozonant wax | by weight 1.0 part by weight | | | |
| e) | same condensation product as c) + anti-ozonant wax | 4.0 parts by weight 2.0 parts by weight | >168 | >168 | >168 | >168 |

EXAMPLE 17

Test mixture and vulcanisation as in Example 16. On this occasion, the ozone concentration was 200 parts of ozone to 100 million parts of air.

Table 7

| Elongation in % | | | 10 | 20 | 35 | 60 |
|---|---|---|---|---|---|---|
| a) | without antiozonant/ without antiozonant wax (comparison) | | <2 | <2 | <2 | <2 |
| b) | antiozonant wax (comparison) | 1.0 part by weight | <2 | <2 | <2 | <2 |
| c) | condensation product of pentaerythritol and 2,5-endomethylene-tetrahydro- Δ³-benzaldehyde in a molar ratio of 1:2 (comparison) | 4.0 parts by weight | <2 | <2 | <2 | <2 |
| d) | same condensation product as c) + anti-ozonant wax | 4.0 parts by weight 1.0 part by weight | >168 | >168 | >168 | <2 |
| e) | same condensation product as c) + anti-ozonant wax | 4.0 parts by weight 2.0 parts by weight | >168 | >168 | >168 | <2 |

We claim:

1. A composition comprising a natural and/or synthetic rubber stabilized with an ozone resistant amount of a condensation product of at least one member selected from the group consisting of triols, tetraols, pentaols and hexaols and a compound of the formula

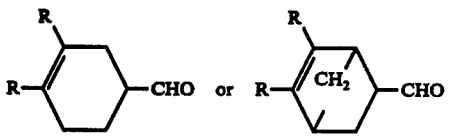

wherein R is the same or different and is hydrogen or methyl, said condensation product being in a molar ratio of 1:1 to 1:3 and having all the aldehyde groups thereof present in acetalated form.

2. The composition of claim 1 wherein the condensation product is the condensation product of a triol with said compound of said formula in a molar ratio of 1:1 or 1:1.5.

3. The composition of claim 1 wherein the condensation product is the condensation product of a tetraol with said compound of said formula in a molar ratio of 1:1 or 1:2.

4. The composition of claim 1 wherein the condensation product is the condensation product of a pentaol with said compound of said formula in a molar ratio of 1:1, 1:1.5, 1:2 or 1:2.5.

5. The composition of claim 1 wherein the condensation product is the condensation product of a hexaol with said compound of said formula in a molar ratio of 1:1, 1:2 or 1:3.

6. The composition of claim 1 wherein said at least one member is selected from the group consisting of glycerol, 1,1,1-trimethylolethane, 1,1,1-trimethylolpropane, 1,1,1-trimethylolbutane, 1,2,6-hexane triol, pentaerythritol, 2,2,6,6-tetramethylol cyclohexanol, sorbitol and mannitol.

7. The composition of claim 1 wherein said compound of said formula is selected from the group consisting of tetrahydro-Δ³-benzaldehyde; 3-methyl-, 4-methyl- and 3,4-dimethyl-tetrahydro-Δ³-benzaldehyde; 2,5-endomethylene tetrahydro-Δ³-benzaldehyde and 3-methyl-, 4-methyl- and 3,4-dimethyl-2,5-endomethylene tetrahydro-Δ³-benzaldehyde.

8. The composition of claim 1 wherein said condensation product is the condensation product of pentaerythritol and tetrahydro-Δ³-benzaldehyde in a molar ratio of 1:2.

9. The composition of claim 1 wherein said condensation product is the condensation product of pentaerythritol and 3-methyl-tetrahydro-Δ³-benzaldehyde.

10. The composition of claim 1 wherein said condensation product is the condensation product of pentaerythritol and 4-methyl-tetrahydro-Δ³-benzaldehyde.

11. The composition of claim 1 wherein said condensation product is the condensation product of pentaerythritol and endomethylene tetrahydro-Δ³-benzaldehyde.

12. The composition of claim 1 wherein said rubber is a polychloroprene rubber with a minimum polychloroprene content of 20% by weight and said condensation product is present in an amount of from 0.1 to 6.0% by weight based on the weight of said rubber.

13. The composition of claim 1 wherein said rubber is other than polychloroprene and said composition contains a hydrocarbon wax in a ratio by weight of wax to condensation product of between 0.25:1 and 2.5:1.

14. The composition of claim 13 wherein said condensation product and said wax are present in an amount of from 0.5 to 15% by weight based on the total rubber content.

15. The composition of claim 13 wherein said condensation product and said wax are present in an amount of from 1 to 10% by weight based on the total rubber content.

16. A composition comprising (a) a condensation product of at least one member selected from the group consisting of triols, tetraols, pentaols and hexaols and a compound of the formula

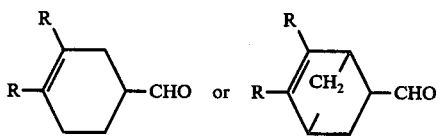

wherein R is the same or different and is hydrogen or methyl, said condensation product being in a molar ratio of 1:1 to 1:3 and having all the aldehyde groups thereof present in acetalated form and (b) a hydrocarbon wax, the weight ratio of said wax to said condensation product being between 0.25:1 and 2.5:1.

17. The composition of claim 16 wherein the condensation product is the condensation product of a triol with said compound of said formula in a molar ratio of 1:1 or 1:1.5.

18. The composition of claim 16 wherein the condensation product is the condensation product of a tetraol with said compound of said formula in a molar ratio of 1:1 or 1:2.

19. The composition of claim 16 wherein the condensation product is the condensation product of a pentaol with said compound of said formula in a molar ratio of 1:1, 1:1.5, 1:2 or 1:2.5.

20. The composition of claim 16 wherein the condensation product is the condensation product of a hexaol with said compound of said formula in a molar ratio of 1:1, 1:2 or 1:3.

21. The composition of claim 16 wherein said at least one member is selected from the group consisting of glycerol, 1,1,1-trimethylolethane, 1,1,1-trimethylolpropane, 1,1,1-trimethylolbutane, 1,2,6-hexane triol, pentaerythritol, 2,2,6,6-tetramethylol cyclohexanol, sorbitol and mannitol.

22. The composition of claim 16 wherein said compound of said formula is selected from the group consisting of tetrahydro-$\Delta^3$-benzaldehyde; 3-methyl-, 4-methyl- and 3,4-dimethyl-tetrahydro-$\Delta^3$-benzaldehyde; 3,5-endomethylene tetrahydro-$\Delta^3$-benzaldehyde and 3-methyl-, 4-methyl- and 3,4-dimethyl-2,5-endomethylene tetrahydro-$\Delta^3$-benzaldehyde.

23. The composition of claim 16 wherein said condensation product is the condensation product of pentaerythritol and tetrahydro-$\Delta^3$-benzaldehyde in a molar ratio of 1:2.

24. The composition of claim 16 wherein said condensation product is the condensation product of pentaerythritol and 3-methyl-tetrahydro-$\Delta^3$-benzaldehyde.

25. The composition of claim 16 wherein said condensation product is the condensation product of pentaerythritol and 4-methyl-tetrahydro-$\Delta^3$-benzaldehyde.

26. The composition of claim 16 wherein said condensation product is the condensation product of pentaerythritol and endomethylene tetrahydro-$\Delta^3$-benzaldehyde.

27. A process for stabilizing a natural and/or synthetic rubber against ozone attack which comprises adding to said rubber an ozone resistant amount of a condensation product of at least one member selected from the group consisting of triols, tetraols, pentaols, and hexaols and a compound of the formula

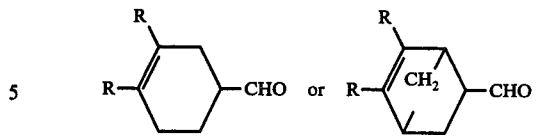

wherein R is the same or different and is hydrogen or methyl, said condensation product being in a molar ratio of 1:1 to 1:3 and having all the aldehyde groups thereof present in acetalated form.

28. The process of claim 27 wherein said condensation product is the condensation product of a triol with said compound of said formula in a molar ratio of 1:1 or 1:1.5.

29. The process of claim 27 wherein said condensation product is the condensation product of a tetraol with said compound of said formula in a molar ratio of 1:1 or 1:2.

30. The process of claim 27 wherein said condensation product is the condensation product of a pentaol with said compound of said formula in a molar ratio of 1:1, 1:1.5, 1:2 or 1:2.5.

31. The process of claim 27 wherein the condensation product is the condensation product of a hexaol with said compound of said formula in a molar ratio of 1:1, 1:2 or 1:3.

32. The process of claim 27 wherein said at least one member is selected from the group consisting of glycerol, 1,1,1-trimethylolethane, 1,1,1-trimethylolpropane, 1,1,1-trimethylolbutane, 1,2,6-hexane triol, pentaerythritol, 2,2,6,6-tetramethylol cyclohexanol, sorbitol and mannitol.

33. The process of claim 27 wherein said compound of said formula is selected from the group consisting of tetrahydro-$\Delta^3$-benzaldehyde; 3-methyl-, 4-methyl- and 3,4-dimethyl-tetrahydro-$\Delta^3$-benzaldehyde; 2,5-endomethylene tetrahydro-$\Delta^3$-benzaldehyde and 3-methyl-, 4-methyl- and 3,4-dimethyl-2,5-endomethylene tetrahydro-$\Delta^3$-benzaldehyde.

34. The process of claim 27 wherein said condensation product is the condensation product of pentaerythritol and tetrahydro-$\Delta^3$-benzaldehyde in a molar ratio of 1:2.

35. The process of claim 27 wherein said condensation product is the condensation product of pentaerythritol and 3-methyl-tetrahydro-$\Delta^3$-benzaldehyde.

36. The process of claim 27 wherein said condensation product is the condensation product of pentaerythritol and 4-methyl-tetrahydro-$\Delta^3$-benzaldehyde.

37. The process of claim 27 wherein said condensation product is the condensation product of pentaerythritol and endomethylene tetrahydro-$\Delta^3$-benzaldehyde.

38. The process of claim 27 wherein said rubber is a polychloroprene rubber with a minimum polychloroprene content of 20% by weight and said condensation product is present in an amount of from 0.1 to 6.0% by weight based on the weight of said rubber.

39. The process of claim 27 wherein said rubber is other than polychloroprene and said composition contains a hydrocarbon wax in a ratio by weight of wax to condensation product of between 0.25:1 and 2.5:1.

40. The process of claim 27 wherein said condensation product and said wax are present in an amount of from 0.5 to 15% by weight based on the total rubber content.

41. The process of claim 27 wherein said condensation product and said wax are present in an amount of from 1 to 10% by weight based on the total rubber content.

* * * * *